(12) United States Patent
Webb

(10) Patent No.: US 11,529,231 B2
(45) Date of Patent: Dec. 20, 2022

(54) HYBRID ACCOMMODATING INTRA-OCULAR LENS AND METHOD OF USE THEREOF

(71) Applicant: OCUMETICS TECHNOLOGY CORP., Abbotsford (CA)

(72) Inventor: Garth T. Webb, Langley (CA)

(73) Assignee: Ocumetics Technology Corp., Abbotsford (CA)

(*) Notice: Subject to any disclaimer, the term of this patent is extended or adjusted under 35 U.S.C. 154(b) by 0 days.

(21) Appl. No.: 17/272,234

(22) PCT Filed: Aug. 29, 2019

(86) PCT No.: PCT/CA2019/051206
§ 371 (c)(1),
(2) Date: Feb. 26, 2021

(87) PCT Pub. No.: WO2020/041890
PCT Pub. Date: Mar. 5, 2020

(65) Prior Publication Data
US 2021/0307897 A1 Oct. 7, 2021

(30) Foreign Application Priority Data

Aug. 30, 2018 (CA) ................... CA 3016143

(51) Int. Cl.
*A61F 2/16* (2006.01)
*G02B 3/14* (2006.01)

(52) U.S. Cl.
CPC .......... *A61F 2/1648* (2013.01); *A61F 2/1635* (2013.01); *G02B 3/14* (2013.01); *A61F 2002/1682* (2015.04)

(58) Field of Classification Search
CPC .... A61F 2/1635; A61F 2/1624; A61F 2/1648; A61F 2002/1681; A61F 2250/0003; A61F 2250/0018; A61F 2250/0019
See application file for complete search history.

(56) References Cited

U.S. PATENT DOCUMENTS

| 4,892,546 A | 1/1990 | Turley |
| 2003/0060878 A1 | 3/2003 | Shadduck |
| 2007/0118216 A1 | 5/2007 | Pynsol |
| 2009/0043384 A1 | 2/2009 | Niwa et al. |
| 2010/0179653 A1 | 7/2010 | Argento et al. |
| 2010/0228344 A1 | 9/2010 | Shadduck |
| 2014/0368789 A1 | 12/2014 | Webb |

FOREIGN PATENT DOCUMENTS

| EP | 0356050 A1 | 2/1990 |
| WO | 0066037 A1 | 11/2000 |
| WO | 2007107589 A1 | 9/2007 |
| WO | 2008101522 A1 | 8/2008 |
| WO | 2013016804 A1 | 2/2013 |

*Primary Examiner* — Javier G Blanco
(74) *Attorney, Agent, or Firm* — Oyen Wiggs Green & Mutala LLP

(57) ABSTRACT

An intra-ocular lens having an air-filled collapsible cavity situated between two optical elements wherein air is transferred from optical regions of the collapsible cavity to its peripheral haptic regions after being compressed by external force.

5 Claims, 5 Drawing Sheets

HYBRID ACCOMMODATING INTRA-OCULAR LENS AND METHOD OF USE THEREOF

REFERENCE TO RELATED APPLICATIONS

This application is a 371 national phase entry of Patent Cooperation Treaty Patent application no. PCT/CA2019/051206 filed 29 Aug. 2019 entitled A HYBRID ACCOMMODATING INTRA-OCULAR LENS AND METHOD OF USE THEREOF, which claims priority to Canadian patent application No. 3016143 filed 30 Aug. 2018. Both of the foregoing applications are hereby incorporated by reference in their entireties for all purposes. The present invention relates to the applicant's inflatable lens/lens retainer as disclosed in international application publication no. WO 2009/021327 entitled INFLATABLE INTRA-OCULAR LENS/LENS RETAINER published Feb. 19, 2009, as well as international application publication no. WO 2014/021391 published Aug. 14, 2014 entitled EXPANDABLE SUSPENSION SYSTEMS FOR INTRA-OCULAR LENSES and international application publication no. WO 2009/021326 entitled PNEUMATIC INTRA-OCULAR LENS published Feb. 19, 2009.

TECHNICAL FIELD

The invention relates to intra-ocular lenses that can change curvature in response to tension exerted by the ciliary muscle/zonule/lens capsule complex upon the natural lens space within the eye.

BACKGROUND

Intra-ocular lenses that have an ability to re-engage the natural kinetics of the ciliary muscle/suspensory ligament/lens capsule complex after lens extraction, allowing the presbyopic eye to recover its ability to shift focus from distance to near, have emerged. Within this competitive field, much attention has focused upon an ability to insert these new lens types through small corneal incisions within the eye.

Presently, liquid-filled intra-ocular lenses, such as the investigational device manufactured by Power Vision Corporation called the Fluid Lens™, exhibit a variety of limitations. Liquid lodged inside these lens types is compressed and transferred to various regions of the device during the daily routine of the eye shifting focus from near to distance. This repetitive action leaves the sealed edges that hold the device together vulnerable to rupture over time. This proclivity is heightened by the tendency of the liquid to erode and weaken the adhesive bonds holding the sealed edges of the device together. Further to this, liquid-filled intra-ocular lenses tend to be bulky and cumbersome to insert, leaving them particularly prone to damage during the insertion process, which entails that they be compressed and shunted through a narrow tubule before being released into the natural lens space within the eye.

Air-filled intra-ocular lenses are thinner than fluid-filled intra-ocular lenses, and as a result are generally easier to insert. They have no liquid to interfere with the integrity of adhesive bonds holding their structural components together; however, they are inherently plagued by internal reflection and glare. In addition to this annoyance, their refractive properties can be potentially altered by even small changes of barometric pressure. In light of the limitations confronting today's accommodating intra-ocular lens design options, there is need for improvement.

The foregoing examples of the related art are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

According to one embodiment, a hybrid intra-ocular lens is provided which includes both solid optical elements and fluid-filled optical elements, such as air filled and which converts from a solid optical element to a partially liquid or air-filled optical element during accommodation. According to one embodiment a partially air-filled intra-ocular lens comprises a hollow air-filled lens compartment encased on one side by a relatively non-deformable optical element which is met at its convex apex by a second optical element that is relatively deformable. The shape profile of the surface of the deformable optical element that contacts the apex of the non-deformable optical element can be of various configurations: flat, convex, concave, multi-focal or aspherical, provided that an air space resides between the remaining portions of the optical elements when the device is in its habitual resting state. The haptics of the two optical elements converge to connect with each other and are bonded together around their perimeters, thereby defining the size and shape of a hollow, air-filled compartment. Just as it is with the two optical elements, the air-filled compartment thereby comprises an optical region and a haptic region.

When the peripheral regions of the optical regions of the two optical elements are pressed together by opposing external force, the deformable optical element bends to conform to the shape of the non-deformable optical element. During this process, the air which normally occupies the space between the two optical regions is displaced outwardly toward the air space between the haptics. When sufficient opposing force is delivered to the optical regions of the two optical elements, their inner surfaces align and connect, with the ability to subsequently separate without adhesion. At this moment, two aspects of the invention are achieved. Firstly, the optical region of the lens pair no longer has an air interface to create internal reflection and glare. Secondly, the eye can remain focused upon distant objects without being influenced by changes of barometric pressure. This process can be achieved with one or both optical elements having deformable properties.

Radial slots may be provided in the lower surface of the deformable optical element surrounding the perimeter of the optical region of the deformable optical element, connected to a circumferential channel in the deformable optical element, to allow air to circulate freely between the optical region and the haptic region of the air-filled compartment. This channel and network of radial slots is an optional feature of the design, which also provides a means for controlling material distortions that can occur when a spherical shell is forced to alter its shape. The width of the radial slots can be selected to alter the flow of air as required.

More particularly, according to one embodiment there is provided a partially air-filled intra-ocular lens comprising a first non-deformable optical element which is sealed around its perimeter to a second deformable optical element forming a sealed air-filled collapsible cavity, the first non-deformable optical element and the second deformable optical element each having central optical regions and first and second haptic regions associated with respective ones of the first non-deformable optical element and the second deformable optical element and each sealingly connected to the other to form the sealed perimeter. The first optical element has a convex shape upon its inner surface with the apex of the convex inner surface pressing against the central region of the deformable optical element leaving a sealed collapsible air space in the remaining area between the optical regions of the first and second optical elements.

According to a further aspect the sealed air-filled collapsible cavity may comprise an optical region, located between the optical regions of the first and second optical elements, and a haptic region located between the optical region and the sealed perimeter of the haptic regions, wherein the air-filled collapsible cavity has at least one opening communicating between the optical region and the haptic region whereby when external force generated by ciliary muscle tension is directed upon the perimeter of the optical regions of the optical elements, the optical region of the air-filled cavity is compressed, thereby evacuating the air within it toward the haptic region of the air-filled cavity through the communicating channels and the optical surfaces of the first and second optical elements, which are thereby compressed against one another, thereby focusing the eye upon distant objects, and whereby the elasticity of the deformable optical element causes the compression to be reduced when the ciliary muscle tension is reduced. According to a further aspect the at least one opening communicating between the optical region and the haptic region may comprise a circular channel interconnecting with a plurality of radial channels.

According to a further aspect a method of providing an accommodating intra-ocular lens for replacement in the lens capsule of an eye is provided by providing a lens having the foregoing features in combination with an intra-ocular structure for transferring the ciliary muscle tension to the lens.

With this present optical configuration, the only moment whereby this lens design is subject to internal reflection and glare is when air enters back into the space between the two optical elements. This glare potential can be reduced when the internal optical surfaces of the two optical elements are constructed with relatively short radii of curvature. It can be further reduced by optical elements oriented within the eye such that the non-deformable optical element is positioned anterior to the deformable optical element.

In addition to the exemplary aspects and embodiments described above, further aspects and embodiments will become apparent by reference to the drawings and by study of the following detailed descriptions. While air is described as the gas contained in the compartment of the hybrid lens, other transparent gases or liquids, referred to collectively as fluids, could be substituted with resulting variation in the refractive indices.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

DESCRIPTION

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive sense. In this description and claims, where the term "fluid" is used it includes air and other gases, and liquids.

Figure 1:
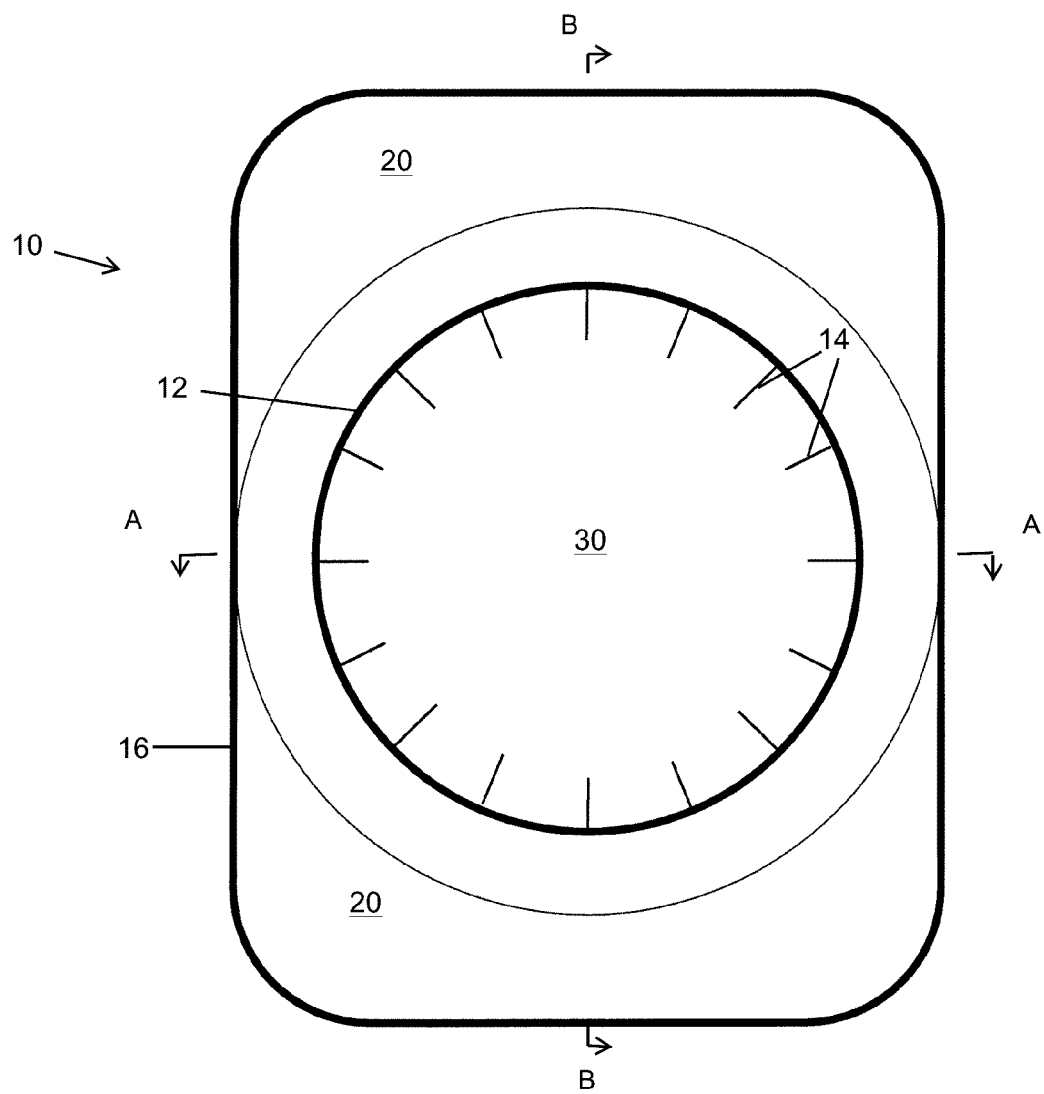
FIG. 1 is a plan view of an air-filled intra-ocular lens according to an embodiment.

FIG. 1 shows a plan view of air-filled intra-ocular lens 10. Intra-ocular lens 10 may be formed of deformable optical element 30 having a central circular transparent optical region and non-deformable optical element 32 having a central circular transparent optical region. Intra-ocular lens 10 may be substantially or completely formed of transparent material. The deformable optical element 30 of intra-ocular lens 10 is circumscribed on its lower surface 33 by circular groove or channel 12. Circular groove or channel 12 is connected to a network of radial slots 14 formed in the lower surface 31 of optical element 30. The perimeter of the intra-ocular lens 10 is circumscribed by seal 16 which seals the outer edges of haptics 20 and 22. The haptics 20, 22 of the deformable and non-deformable optical elements 30, 32 respectively of intra-ocular lens 10 extend between seal 16 and channel 12.

Figure 2:
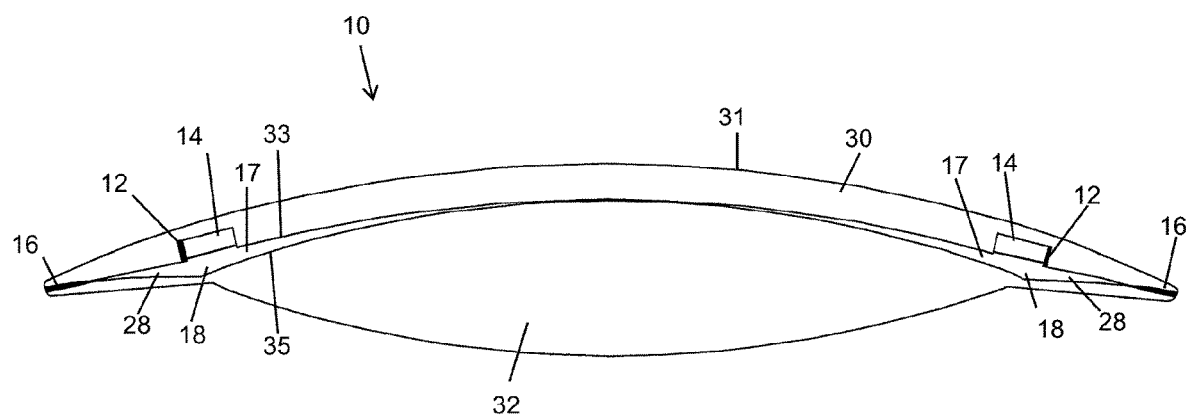
FIG. 2 is a detail cross-sectional view taken along lines A-A of FIG. 1 showing the intra-ocular lens in its resting or low-energy configuration, focusing the eye upon near objects.
Figure 4:
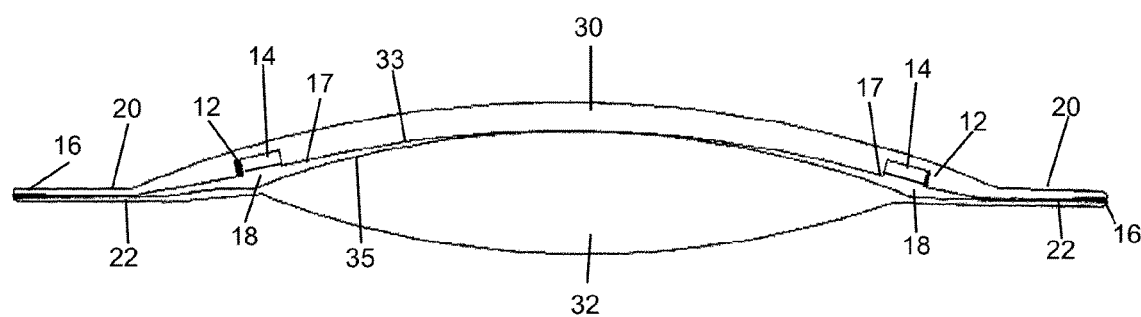
FIG. 4 is a detail cross-sectional view taken along lines B-B of FIG. 1 showing the intra-ocular lens in its resting or low-energy configuration, focusing the eye upon near objects.

FIG. 2 shows a cross-sectional view taken along lines A-A of FIG. 1 of the air-filled intra-ocular lens 10 in its accommodated or resting state, focusing the eye upon near objects. In that state the deformable optical element 30 and non-deformable optical element 32 only come into contact at the apex 40 of the non-deformable optical element 32. Similarly this is shown in FIG. 4 which is a cross-sectional view taken along lines B-B of FIG. 1 of the air-filled intra-ocular lens 10 in its accommodated or resting state.

Figure 3:
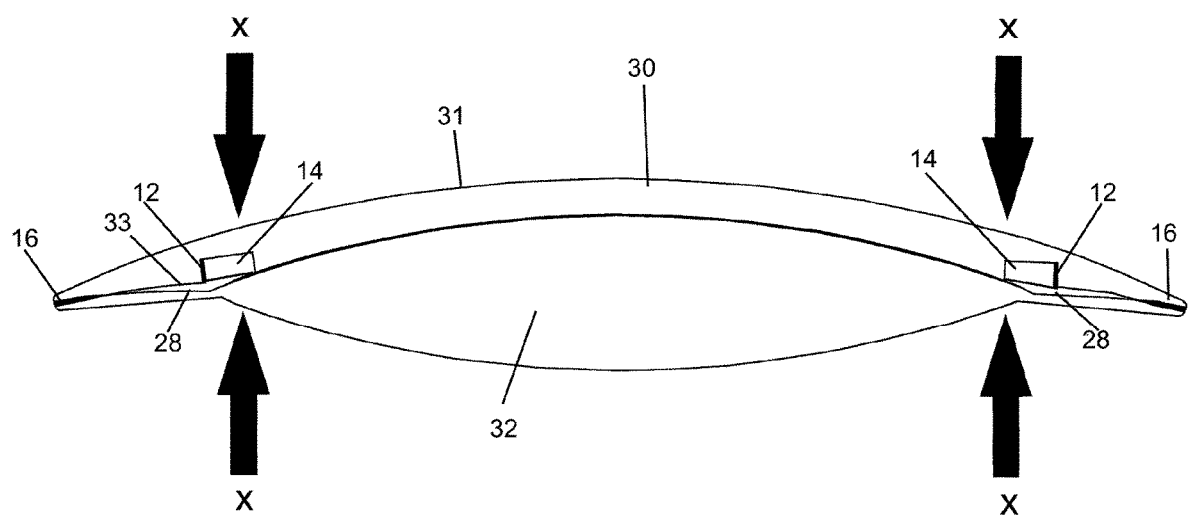
FIG. 3 is a detail cross-sectional view taken along lines A-A of FIG. 1 showing the intra-ocular lens in its compressed or high-energy configuration, focusing the eye upon distant objects.

FIG. 3 shows a cross-sectional view taken along lines A-A of FIG. 1 of air-filled intra-ocular lens 10 wherein. force vectors X are applied upon intra-ocular lens 10 by the ciliary muscles (as described in the referenced international application publication no. WO 2009/021327 entitled "INFLATABLE INTRA-OCULAR LENS/LENS RETAINER") to accommodate the lens to focus on distant or close objects.

In operation, the accommodated configuration, which is shown in FIG. 2, represents the habitual low-energy state of intra-ocular lens 10. The presence of air within the optical region of annular air-filled compartment 18 serves as an "air-lens". When deformable optical element 30 bends to conform to the shape of the upper surface 35 of non-deformable optical element 32 in response to external force as shown by force vectors X in FIG. 3, the inner surface 33 of the deformable optical element 30 becomes more concave while at the same moment, the outer surface 31 becomes more convex. These corresponding curvature changes nullify the refractive impact of each other. However, at the same time that the shape of deformable optical element 30 changes, the shape of the air-lens 18 trapped between the optical elements 30, 32 becomes correspondingly more concave and the shape of the liquid aqueous interface in apposition with the outer surface 31 of deformable optical element 30 becomes likewise, more convex. The difference of the refractive indices of the air-lens/optical element interface is over two and one-half times greater than that of the aqueous/optical element interface. Consequently, as the convexity of the outer surface 31 of deformable optical element 30 increases (as it does in its high energy configuration shown in FIGS. 3 and 5), the result is a significant reduction of the over-all dioptric lens power. Thus, an apparent paradox is revealed; the eye becomes focused upon distant objects when the center thickness of the intra-ocular lens increases.

Figure 5:
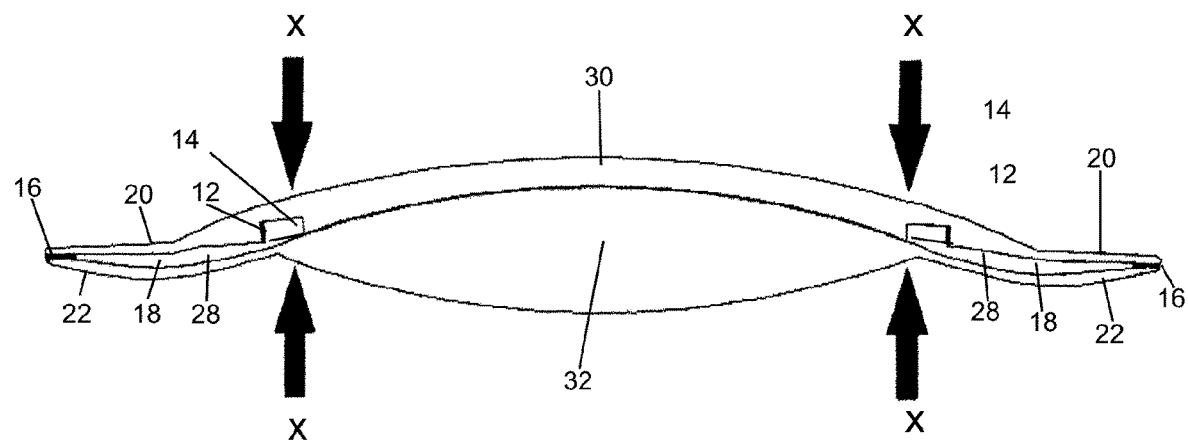
FIG. 5 is a detail cross-sectional view taken along lines B-B of FIG. 1 showing the intra-ocular lens in its compressed or high-energy configuration, focusing the eye upon distant objects.
Figure 6:
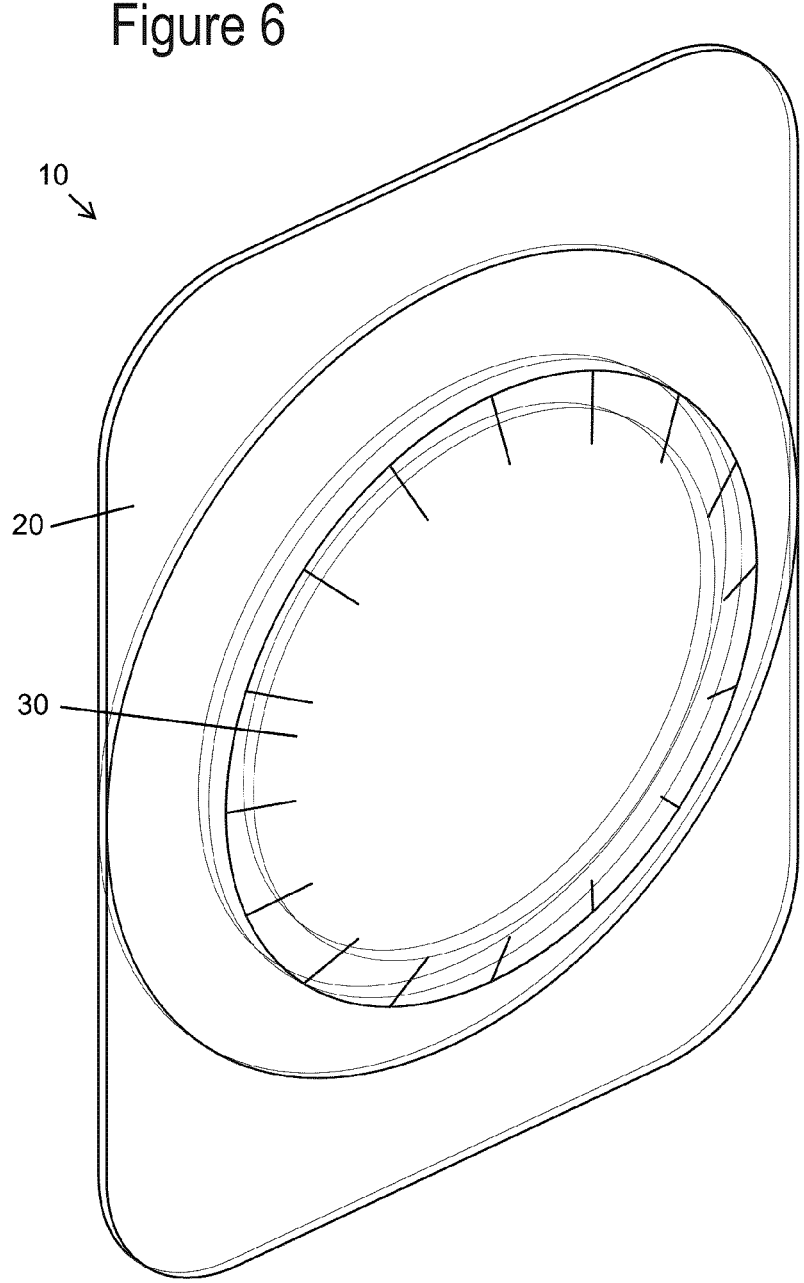
FIG. 6 is a top left perspective view of the air-filled intra-ocular lens shown in FIG. 1.
Figure 7:
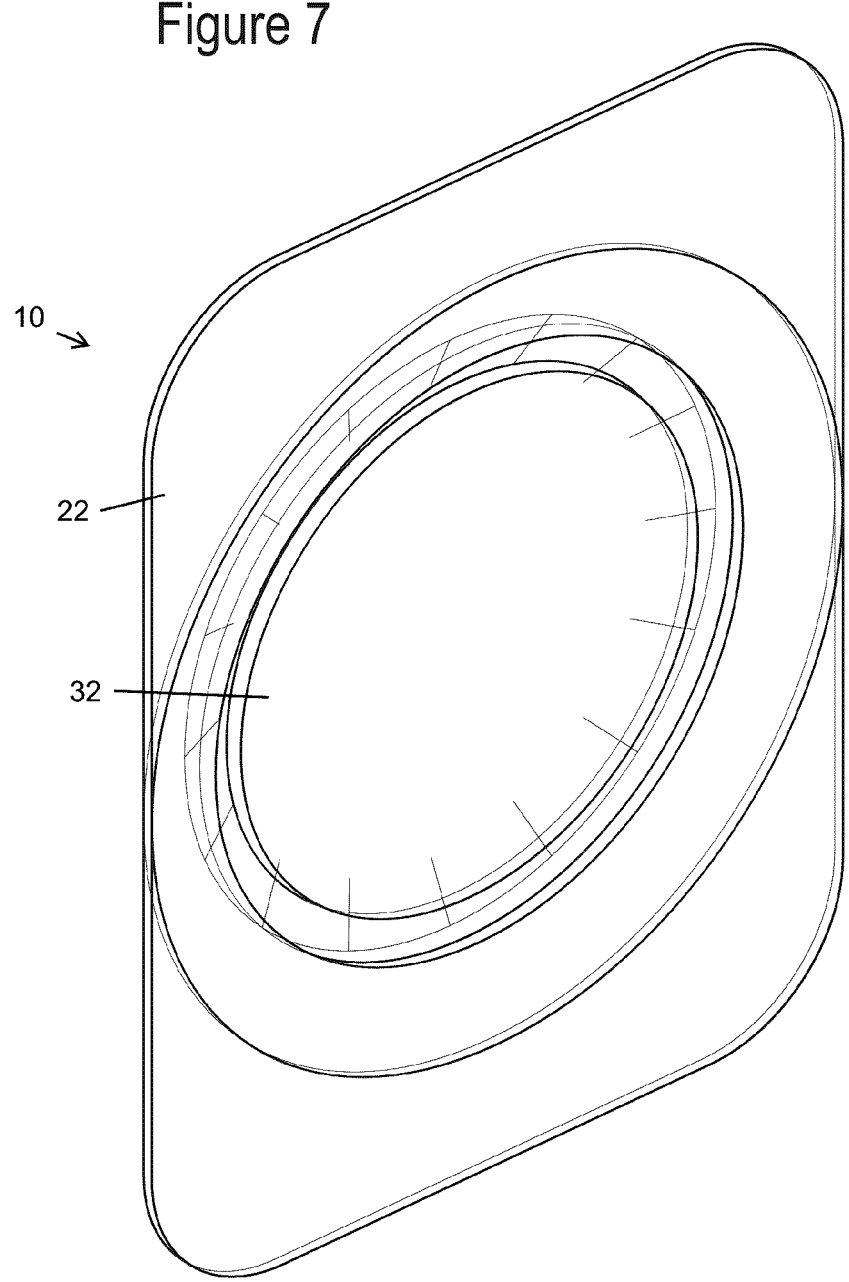
FIG. 7 is a bottom left perspective view of the air-filled intra-ocular lens shown in FIG. 1.

As shown in cross-section in FIG. 2 through 5, air evacuated from the optical region 17 of air-filled compartment 18 is transferred to the haptic region 28 of air-filled compartment 18 when the optical region of deformable optical element 30 is compressed by external force, which is represented in FIGS. 3 and 5 by force vectors X. During this process, the air which normally occupies the space 17 between the lower surface 33 of optical region 30 and upper surface 35 of optical region 32 is displaced outwardly towards the air space 28 between the haptics 20, 22. When sufficient opposing force is delivered to the optical regions of the two optical elements 30, 32, their inner surfaces 33, 35 align and connect, collapsing space 17 with the ability to subsequently separate without adhesion to recreate space 17. At this moment, two aspects of the invention are achieved. Firstly, the optical region of the lens pair no longer has an air interface to create internal reflection and glare. This glare potential can be reduced when the opposed optical surfaces 33, 35 of the two optical elements 30, 32 are constructed with relatively short radii of curvature. It can be further reduced by optical elements oriented within the eye such that the non-deformable optical element is positioned anterior to the deformable optical element. Secondly, the eye can remain focused upon distant objects without being influenced by changes of barometric pressure. This process can also be achieved with both optical elements 30, 32 having deformable properties. The elasticity of the deformable optical element 30 causes the compression to be reduced when said ciliary muscle tension is reduced, causing surfaces 333 and 35 to return to the resting state focusing the eye upon near objects.

Rapid and even transfer of the air from the periphery of the optical region of deformable optical element 30 in the vicinity of surface 33 is enabled by radial slots 14 which carry the air to channel 12 after which it is evenly distributed via circular channel 12 around the annular haptic region 28 of air-filled compartment 18. Radial slots 14 connected to a circumferential channel 12 thus may surround the perimeter of the optical region of optical element 30 to allow air to circulate freely between the optical region 17 and the haptic region 28 of the air-filled compartment 18. Alternatively or in addition the radial slots 14 or circumferential channel 12 or both may be formed in the upper surface of the perimeter of the optical region of non-deformable optical element 32 to similarly allow air to circulate freely between the optical region 17 and the haptic region 28 of the air-filled compartment 18. This channel and network of radial slots is an optional feature of the design, which also provides a means for controlling material distortions that can occur when a spherical shell is forced to alter its shape. The width of the radial slots 14 and channel 12 can be selected to alter the flow of air as required.

Various shapes of the optical surfaces lining the hollow cavity can be selected to match specific optical requirements of any individual eye to tune the optical resolution of the image focused within the eye or to extend the eye's focal range.

The cross-sectional shape profile of the deformable optical element 30 can be customized to accelerate its shape recovery time. For example, the shape profile of the lower surface 33 of the deformable optical element 30 that contacts the upper surface 33 of the non-deformable optical element 32 at its apex can be of various configurations: flat, convex, concave, multi-focal or aspherical, provided that an air space resides between the remaining portions of the optical elements when the device is in its habitual resting state.

Supple supportive structures can be installed upon the perimeter of the optical regions of either of the two optical interfaces to reduce the risk of suction or adhesions between them, which could potentially bind their optical surfaces together immobilizing the movement of deformable optical element 30.

While in the embodiment illustrated in FIGS. 2 and 4 the deformable optical element 30 and non-deformable optical element 32 while in the resting state only come into contact at the apex 40 of the non-deformable optical element 32, in other embodiments the point of contact in the resting state could be located elsewhere than in the central apex of the optical elements, for example on a periphery. See for example the structure illustrated in the applicant's international application, publication no. WO 2013/126986 A1 entitled "Method and Apparatus for Modulating Prism and Curvature Change of Refractive Interfaces" which is incorporated herein by reference.

Materials required for the construction of the optical elements are elastic with strong memory characteristics, readily resuming their original size and shape after being compressed, stretched or otherwise deformed. Materials commonly used for intra-ocular lens fabrication having good shape memory characteristics include but are not limited to the following classifications: silicones, silicone hydro-gels, hydrophobic and hydrophilic acrylics, polyethylene, polypropylene, polyurethane and co:block polymers of these.

The overarching intent for the present invention is to remove and replace an air optical interface within the optical region of an intra-ocular lens as required to allow the human eye to recover its inherent ability to efficiently and predictably shift focus from distance to near and all points between.

While a number of exemplary aspects and embodiments have been discussed above, those of skill in the art will recognize certain modifications, permutations, additions and sub-combinations thereof. For example while air has been described as the fluid contained in the compartment 18, other transparent gases or liquids could be substituted with resulting variation in the refractive indices. It is therefore intended that the following appended claims and claims hereafter introduced are interpreted to include all such modifications, permutations, additions and sub-combinations as are consistent with the broadest interpretation of the specification as a whole.

The invention claimed is:

1. partially air-filled intra-ocular lens comprising a first non-deformable optical element which is sealed around its perimeter to a second deformable optical element forming a sealed air-filled collapsible cavity between said first and second optical elements, said first non-deformable optical element and said second deformable optical element each having central transparent optical regions and first and second haptic regions associated with respective ones of said first non-deformable optical element and said second deformable optical element and each sealingly connected to the other to form said sealed perimeter, wherein said first non-deformable optical element has a convex shape upon its upper surface with a central contact region of said convex upper surface pressing against a central contact region of said deformable optical element leaving an air space in the remaining area between the optical regions of said first and second optical elements, wherein said sealed air-filled collapsible cavity comprises an optical region, located between said optical regions of said first and second optical elements, and a haptic region located between said optical region and said sealed perimeter of the haptic regions of said first and second optical elements, wherein said air-filled collapsible cavity has at least one channel communicating between said optical region and said haptic region whereby when external force generated by ciliary muscle tension is directed upon the perimeter of the optical regions of said first and second optical elements, said optical region of said sealed air-filled collapsible cavity is compressed, thereby evacuating fluid within it toward the haptic region of said sealed air-filled collapsible cavity through said at least one communicating channel and a lower surface of said second deformable optical element is compressed against an upper surface of said non-deformable optical element, thereby focusing the eye upon distant objects, and whereby the elasticity of said deformable optical element causes said compression to be reduced when said ciliary muscle tension is reduced.

2. The intra-ocular lens of claim 1 wherein said contact region of said convex upper surface of said first optical element pressing against a contact region of said deformable optical element is an apex of said convex upper surface of said first optical element.

3. The intra-ocular lens of claim 1 wherein said at least one communicating channel between said optical region and said haptic region of said sealed fluid-filled collapsible cavity comprises a circular channel formed in the lower surface of said deformable optical element interconnecting with a plurality of radial channels formed in the lower surface of said deformable optical element.

4. The intra-ocular lens of claim 1 wherein said at least one communicating channel between said optical region and said haptic region of said sealed fluid-filled collapsible cavity comprises a circular channel formed in the upper surface of said non-deformable optical element interconnecting with a plurality of radial channels formed in the upper surface of said non-deformable optical element.

5. The intra-ocular lens of claim 1 wherein the upper convex surface of said first non-deformable optical element and the lower surface of said second deformable optical element are constructed with short radii of curvature.

* * * * *